United States Patent [19]

Hasselkus

[11] Patent Number: 5,714,505
[45] Date of Patent: Feb. 3, 1998

[54] METHOD FOR TREATMENT OF PSORIASIS, BY OMEPRAZOLE OR RELATED COMPOUNDS

[75] Inventor: Wolfgang Hasselkus, Rödental, Germany

[73] Assignee: Astra Aktiebolag, Sodertalje, Sweden

[21] Appl. No.: 666,504

[22] PCT Filed: Jan. 5, 1994

[86] PCT No.: PCT/SE94/00006

§ 371 Date: Jun. 24, 1996

§ 102(e) Date: Jun. 24, 1996

[87] PCT Pub. No.: WO95/18612

PCT Pub. Date: Jul. 13, 1995

[51] Int. Cl.⁶ .................................................. A61K 31/44
[52] U.S. Cl. ............................................................. 514/338
[58] Field of Search ................................. 514/299, 338

[56] References Cited

FOREIGN PATENT DOCUMENTS 0247983  1/1993  European Pat. Off. .

OTHER PUBLICATIONS

Hasselkus, W. "Afheilung einer chronischen Psoriasis vulgaris unter Omeprazol", Deutsche Med. Wochenschr (Germany) 118 (1–2): 46, 1993.

*Primary Examiner*—Phyllis G. Spivack
*Attorney, Agent, or Firm*—White & Case

[57] ABSTRACT

A method for treatment of psoriasis is disclosed comprising administration of a therapeutically effective dosage of omeprazole.

9 Claims, No Drawings

METHOD FOR TREATMENT OF PSORIASIS, BY OMEPRAZOLE OR RELATED COMPOUNDS

FIELD OF INVENTION

The present invention relates to a novel method of treating psoriasis.

BACKGROUND OF THE INVENTION

Psoriasis is a primary disease of the skin characterized by well-demarcated, inflammatory papules and plaques, which are typically covered by thickened scales. It is a disease of increased proliferation of epidermal cells, the precise cause of which is unknown.

The incidence of psoriasis in e.g. the U.S. is about 2%. About 3% of whites and 1% of blacks are affected.

Therapeutic efforts in psoriasis are aimed at decreasing the proliferative rate of the epidermis either by direct action on cell division, or through agents that reduce the inflammatory response or vascular permeability. For patients with localised, limited psoriasis, topical administration of calcipotriol (D-vitamin derivative), dithranol or corticosteroids are the most convenient outpatient therapy. For patients with more extensive disease topical treatment followed by eradication with UV light may be necessary.

For patients with extensive disease a systemic antimitotic agent, such as methotrexate, can be used.

Extensive psoriasis can also be treated with photochemotherapy. In this regimen, orally administered, 8-methoxypsoralen produces photosensitization, which is followed by exposure to ultraviolet A (PUVA, 320 nm).

The retinoids, particularly eretrinate, either alone or in combination with PUVA, are also effective treatment for psoriasis. Furthermore, during acute attacks of pustular psoriasis, systemic steroids have been the therapy of choice.

In view of postulated immunologic mechanisms it is interesting that cyclosporin A has been shown to be an effective treatment. Considering the risk for complications, such treatment should, however, be reserved for patients with recalcitrant, debilitating psoriasis when the benefit outweighs the potential risk of complications.

As will be clear from the above, there is a need for new, alternative and improved methods for treating psoriasis. The present invention provides a novel method for the treatment of psoriasis.

DETAILED DESCRIPTION OF THE INVENTION

It has been found according to the invention that administration of omeprazole to patients affected by psoriasis results in disappearance of or great improvement of the symptoms of psoriasis. This applies to all manifestations of psoriasis.

Omeprazole is a pharmaceutical agent having the formula

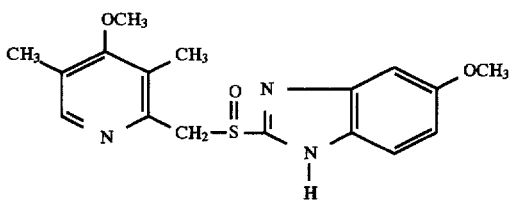

and is used in therapy for treatment of gastric acid related diseases, such as gastric ulcer.

Omeprazole can be administered orally, rectally or parenterally in neutral form or in the form of a basic salt, such as the $Mg^{2+}$, $Ca^{2+}$, $Na^+$, or $K^+$ salts, preferably the $Mg^{2+}$ or $Na^+$ salts. While the effect on the symptoms of psoriasis have been established in patients who have taken omeprazole by the oral route, it is believed that the effect of omeprazole on psoriasis is a systemic effect which is not dependent on what mode of administration that is used, and that accordingly the healing effect on psoriasis will be seen also with other routes of administration such as rectal or parenteral administration.

Omeprazole can also be used in the form of a substantially pure enantiomer, or a salt thereof such as the salts mentioned above.

The commercially available pharmaceutical formulations of omeprazole will normally be used also for the use of omeprazole for treating psoriasis. Examples of such commercially available formulations are:

pellets of omeprazole, packaged in capsules tablet containing omeprazole as active ingredient solutions for parenteral administration, comprising e.g. the sodium salt of omeprazole as active ingredient.

Being a labile compound with poor storage stability at neutral or acid pH, omeprazole formulations must be produced with great care. Examples of ways of producing stable formulations are given in e.g. EP-A-247,983.

The dose of omeprazole to be administered at treatment of psoriasis will vary depending on factors such as the severity of the disease and the status of the patient. The dosage range at oral, rectal as well as i.v. administration may be in the interval from 1 to 100 mg per day. Normally, an amount of from 10 to 40 mg of omeprazole a day is envisaged at oral administration. A particularly suitable dosage may be in the range of 10–20 mg omeprazole per day.

Other compounds which can be used in the treatment of psoriasis in the same manner as omeprazole are the following:

H 259/31

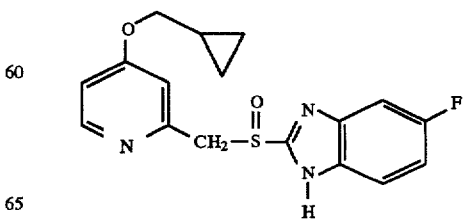

tration are H 259/31, H287/23, lansoprazole, pantoprazole, E-3810, TU-199 and TY-11345. Dosages to be administered can be in the same ranges as given above for omeprazole.

The invention is further exemplified by the following case studies. During oral treatment with omeprazole for acid related diseases, evidence has accumulated that omeprazole may be beneficial for treatment of psoriasis. Some examples are presented below:

Case 1—70-Year-Old Woman

A 70 year old woman suffered since 53 years from typical chronic psoriasis vulgaris with main areas at both wrists as well as on her back. Treatment was, on basis of advice from her doctor, carried out with different gluco corticosteroids containing ointments as well as with salicyl-vaselin. However, the chronic state not changed.

Because of reflux esophagitis, degree III, the patient was treated since two years with omeprazole, once daily, 40 mg, evenings. After 3 weeks the patient noted for the first time the start of an improvement of her psoriasis. After 2 months, a clear improvement of the skin areas was established, an improvement which 2 years afterwards still was present. Already since the beginning of the improvement the patient used no external medicaments any longer.

Case 2—70-Year-Old Man

Simultaneous disease: porphyria cutanea tarda. Widespread psoriasis in his whole life, partly controlled with topical treatment and PUVA treatment.

Because of acid-related disease treatment with ranitidin was initiated and due to lack of efficacy the treatment was, after a few months, changed to omeprazole. During one month's treatment with omeprazole the psoriatic condition improved considerably, but flared up again when the treatment was changed back to ranitidin. The condition improved again when omeprazole was re-instituted and the patient is currently under treatment with omeprazole for his psoriasis.

Case 3—A 70-Year-Old Man with omeprazole since many years. Also father and sister have had psoriasis. The condition has been treated topically, but has never been completely controlled, especially not in the hair bottom.

When treatment with omeprazole was started because of a bleeding ulcer the psoriatic lesions healed completely, including the changes in the hair bottom, which was noted spontaneously by the barber. The psoriatic lesions returned when the omeprazole treatment was stopped.

Case 4—A 60-Year-Old Lady with long-standing history of psoriasis. Whilst on omeprazole over a 3 month period there was a total and complete eradication of her psoriasis not only of the skin but of the finger nails. When omeprazole was stopped the condition started to recur.

Case 5—A Lady, Age Not Known who has been treated for severe psoriasis for some years. She has needed systemic treatment at times but has never really been clear of skin lesions. When treatment with omeprazole was started because of a gastric ulceration, her psoriasis started to clear up over a 5-week period.

What is claimed is:

1. A method for treatment of psoriasis comprising administration of a therapeutically effective dose of omeprazole.

Where applicable, a compound listed above may be used in racemic form or in the form of a substantially pure enantiomer. The compounds listed may be used in the same manner as described above for omeprazole, i.e. be administrated orally, rectally as well as parenterally. Parenteral administration is feasible provided that the compound is water soluble. Suitable compounds for parenteral adminis- 2. A method according to claim 1, wherein omeprazole is administered orally.

3. A method according to claim 1, wherein omeprazole is administered parenterally.

4. A method according to claim 1, wherein omeprazole is administered rectally.

5. A method according to claims 1–3 or 4, wherein omeprazole in neutral form is administered.

6. A method according to claim 1, wherein omeprazole is administered in the form of a basic salt.

7. The method according to claim 6 wherein the basic salt is a magnesium salt or a sodium salt.

8. A method according to claim 1, wherein omeprazole is administered in a dose of from 1 to 100 mg per day.

9. A method according to claim 8 wherein omeprazole is administered in a dose of from 10 to 40 mg per day.

* * * * *